US005478325A

United States Patent [19]

Fu-Hsiang

[11] Patent Number: 5,478,325

[45] Date of Patent: Dec. 26, 1995

[54] SOLUTION FEEDER WITH A NIPPLE

[76] Inventor: Chen Fu-Hsiang, 47-14, Fan-po Street, Fan-po Village, Fu-Hsin Hsiang, Chang Hwa Hsien, Taiwan

[21] Appl. No.: 381,302

[22] Filed: Jan. 31, 1995

[51] Int. Cl.$^6$ .......... A61M 5/178

[52] U.S. Cl. .......... 604/212; 215/11.1; 604/77

[58] Field of Search .......... 604/77, 27, 73, 604/79, 187, 181, 212, 217, 218, 38; 606/234, 235, 236; 215/11.1, 11.3

[56] References Cited

U.S. PATENT DOCUMENTS

| | | | |
|---|---|---|---|
| 1,366,727 | 1/1921 | Gerstner | 215/11.1 |
| 1,545,436 | 7/1925 | McGeary | 215/11.1 |
| 4,411,656 | 10/1983 | Cornett, III | 604/212 |
| 4,753,638 | 6/1988 | Peters | 604/212 |
| 4,813,556 | 3/1989 | Lawrence | 215/11.1 |
| 5,024,341 | 6/1991 | Dekerle | 215/11.1 |
| 5,242,422 | 9/1993 | Schneberger et al. | 604/212 |
| 5,354,274 | 10/1994 | Demeter et al. | 604/77 |

*Primary Examiner*—Corrine M. Maglione
*Assistant Examiner*—N. Kent Gring
*Attorney, Agent, or Firm*—Larson and Taylor

[57] ABSTRACT

A solution feeder with a nipple includes a bottle a nipple, an inner rod and a cylindrical cap. The bottle is made of a soft elastic material and compressible to force solution contained therein to flow up through several passageways formed between the nipple and several ribs of the inner rod and through a hole in the top of the nipple into the mouth of the user even if the user resists chewing and bites the nipple.

3 Claims, 2 Drawing Sheets

SOLUTION FEEDER WITH A NIPPLE

BACKGROUND OF THE INVENTION

This invention relates to a solution feeder with a nipple, particularly one that can forcibly make the solution contained in a bottle flow into the mouth of a user, i.e. a baby, even if the user resists chewing the nipple.

A known conventional feeder has a spoon-shaped head instead of a nipple to receive the solution contained in a bottle and then for a user to drink. However, the spoon-shaped head is open so that the solution received therein is liable to drop out in case of the user's resistance.

Another known conventional feeder has a bottle, an annular cap, a nipple, a cone-shaped annular nipple supporter, a ring fixed around an upper portion of the nipple supporter, and a soft sack positioned in a center hollow of the nipple supporter. The nipple supporter has the upper and the lower end of its center hollow provided with a leaking hole for the solution contained in the bottle to drip out of the nipple. Provided a user should resist to chew the nipple and bites the nipple with force, the solution would not flow out of the nipple.

SUMMARY OF THE INVENTION

In order to solve the problems in the art mentioned above, the present invention has been worked out to provide a solution feeder with a nipple comprising a bottle, and a nipple for a user to chew to drink the solution contained in the bottle. In case that the user resists chewing, the elastic bottle can be compressed to force the solution to flow through passageways formed between an inner rod positioned in the nipple and the nipple to flow out of the nipple into the mouth of the user even if the user should resist and bite the nipple.

BRIEF DESCRIPTION OF DRAWINGS

This invention will now be described in detail with reference to accompanying drawings wherein.

DETAILED DESCRIPTION OF THE INVENTION

Figure 1:
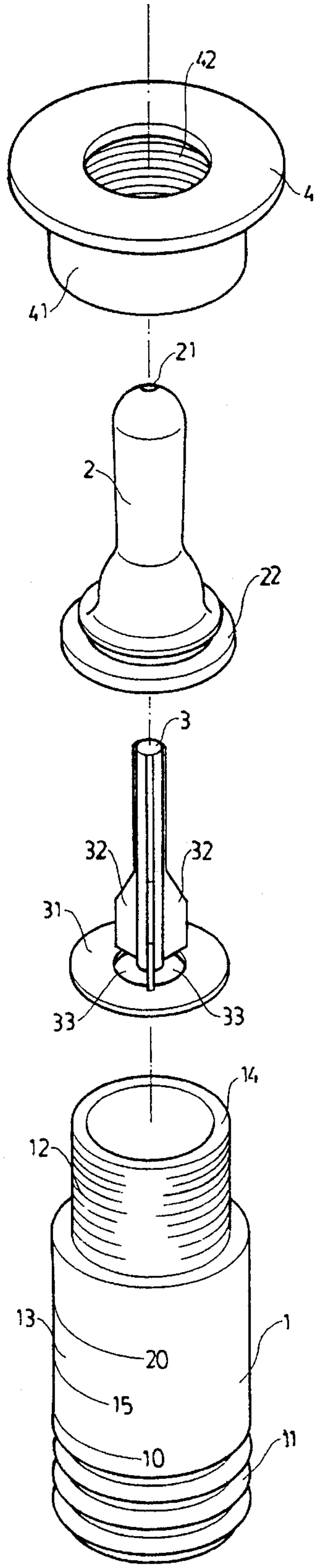
FIG. 1 is an exploded perspective view of a solution feeder with a nipple in the present invention.

A preferred embodiment of a solution feeder with a nipple in the present invention, as shown in FIG. 1, comprises a bottle 1, a nipple 2, an inner rod 3 and a cylindrical cap 4 as main components combined together.

The bottle 1 is made of a soft elastic material, having a compressible portion 11 to be compressed up and down so that the dimensions of the bottle 1 may be reduced, and thus the solution contained in the bottle 1 may be forcibly pressed out of the bottle 1. The outer surface of the bottle is marked with several numbers to indicate the quantity of the solution contained in the bottle 1.

An upper portion of the bottle 1 has its outer surface provided with a thread 12 to engage with an inner thread of the cylindrical cap 4 so as to combine the nipple 2 on top of the bottle 1.

The nipple 2 is the same as a conventional nipple, having a hole 21 in the top for the solution in the bottle 1 to flow out, and positioned on top of the bottle 1 by means of the cylindrical cap 4 after the cap 4 is screwed with the upper threaded portion 12 of the bottle 1, with a cylindrical portion of the nipple 2 passing through a center hole of the cap 4 and projecting up. The nipple 2 also has a bottom ring 22 with a larger diameter than the rest portion of the nipple 2 does.

The inner rod 3 is to extend lengthwise in an interior of a chewing portion of the nipple 2, having a large diameter ring 31 at the bottom, several vertical ribs 32 projecting out radially or irregularly from a lengthwise body of the inner rod 3. The ring 31 is positioned on top of the bottle 1 as the bottom ring 22 of the nipple 2 is. The ribs 32 have their bottom ends fixed firmly on the ring 31, forming several through holes 33 between the rod 3 and the ring 31. The length of the rod 3 is a little shorter than that of the nipple 2, leaving the top of the rod 3 separated from the hole 21 of the nipple 2 with a proper distance to prevent the hole 21 from becoming blocked.

The cylindrical cap 4 has a cylindrical portion 41 with an inner thread 42 to engage with the threaded portion 12 of the bottle 1, a center hole for the chewing portion of the bottle 1 to pass through upward, and an annular upper rim of a larger diameter than that of the nipple 2 for the lip of a baby user to contact with so as to prevent the nipple 2 from being chewed too deeply by a baby user.

Figure 2:
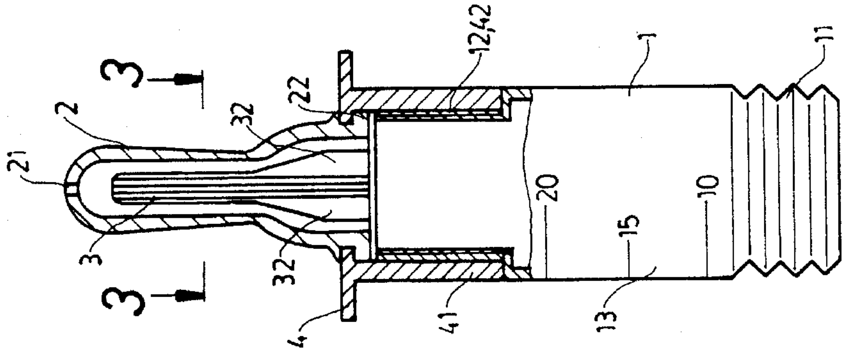
FIG. 2 is a partial cross-sectional view of the solution feeder with a nipple in the present invention.

FIG. 2 shows the condition of this solution feeder completely combined together, and a medicinal solution is to be poured in the bottle 1, then the cylindrical cap 4, the nipple 2, and the inner rod 3 are to be combined on top of the bottle 1.

Figure 3:
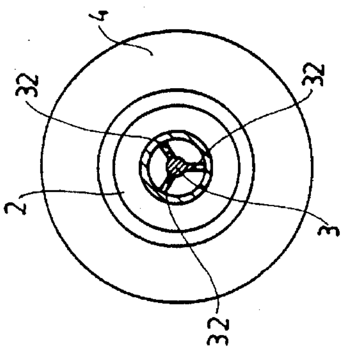
FIG. 3 is a cross-sectional view taken along line 3—3 of FIG. 2.
Figure 4:
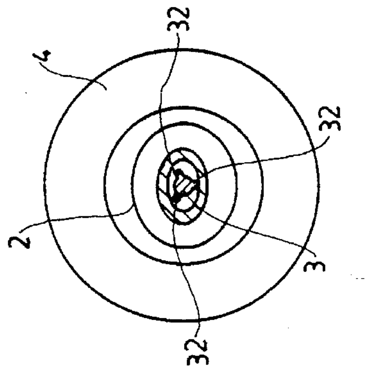
FIG. 4 is a cross-sectional view of a nipple bitten in the present invention.

FIG. 3 shows the condition of the chewing portion of the nipple 2 while it is not yet chewed by a user. In the course of user's chewing the chewing portion of the nipple 2 may be disfigured, but not tightly contact with the outer surface of the inner rod 3, prevented by the ribs 32 thereof. Therefore, several gaps are formed between the nipple 2 and the inner rod 3, permitting the medicinal solution to flow through upward to pass through the hole 21 of the nipple 2, provided the bottle 1 is compressed repeatedly.

A special feature of the present invention is the inner rod 3 positioned in the interior of the nipple 2 for hampering the nipple 2 from completely being blocked due to biting or hard chewing. And the ribs 32 can be displaced by other equivalents such as grooves regularly or irregularly provided, as long as they can form gaps between the nipple 2 and the inner rod 3 for the solution in the bottle to pass through. Then, they can be deemed to be the same art of the present invention.

The structure of the solution feeder in the present invention never gives rise to the problem of chewing the nipple 2 too deep to hurt the throat of a baby user in practical use. Even if a user should resist chewing and bites the nipple 2, the medicinal solution can still be forced to flow through the holes 33 of the ring 31 and the hole 21 of the nipple 2 by means of compressing the bottle 1. And in addition, the inner rod 3 can be taken off together with the cylindrical cap 4, without need of directly catching hold of the rod 3 manually, preventing it from being contaminated in handling the nipple 2, the inner rod 3, and the cylindrical cap 4.

What is claimed is:

1. A solution feeder comprising:

a nipple including an upper chewing portion having a hole therein and a lower portion;

a bottle comprising an open top, a threaded neck portion and a lower portion comprising an elastic material compressible along a longitudinal axis of the bottle for reducing a height of the bottle and forcing solution to flow out of the open end of the bottle;

a cylindrical cap for attaching the lower portion of the nipple to the open top of the bottle, the cap having a threaded portion for engaging the threaded neck portion of the bottle;

an inner rod extending into the chewing portion of the nipple, the inner rod including passageways for the flow of solution from the bottle to the hole, a top end of the inner rod being separated from the hole; and a ring attached to a bottom end of the inner rod for supporting the inner rod in the nipple, said ring being held in place at the open top of the bottle by the cylindrical cap, the ring having an outer diameter sufficient to prevent the ring from entering the threaded neck portion.

2. The solution feeder according to claim 1 wherein the passageways are formed by vertical ribs projecting radially outwards from the inner rod.

3. The solution feeder according to claim 1 wherein the passageways are formed by grooves in the inner rod.

* * * * *